United States Patent [19]

Peterson et al.

[11] 4,304,135

[45] Dec. 8, 1981

[54] CONSTRAINT FACTOR FOR STRUCTURAL MONITORING

[75] Inventors: Marvin L. Peterson; Norman W. Hein, Jr.; Donald H. Oertle; Steven E. Hawkins, all of Ponca City, Okla.

[73] Assignee: Conoco Inc., Ponca City, Okla.

[21] Appl. No.: 140,940

[22] Filed: Apr. 16, 1980

[51] Int. Cl.³ .............................................. G01N 19/08
[52] U.S. Cl. ...................................................... 73/799
[58] Field of Search ................. 73/799, 786, 760, 767, 73/772, 802, 803

[56] References Cited

U.S. PATENT DOCUMENTS

| | | | |
|---|---|---|---|
| 3,136,154 | 6/1964 | Christensen | 73/767 |
| 3,596,269 | 7/1971 | Laska | 73/767 |
| 3,786,679 | 1/1974 | Crites | 73/767 |
| 3,845,657 | 11/1974 | Hall et al. | 73/769 |

Primary Examiner—Anthony V. Ciarlante
Attorney, Agent, or Firm—Cortlan R. Schupbach, Jr.

[57] ABSTRACT

A dual element strain gauge is placed near a welded or otherwise constrained joint on a structural member so as to provide a constraint factor. The location for the strain gauge must be selected to provide constraint factor that is preferably near either maximum or minimum value. The strain gauge is monitored to detect a change in the initial constraint factor, which indicates failure has begun or is imminent.

18 Claims, 7 Drawing Figures

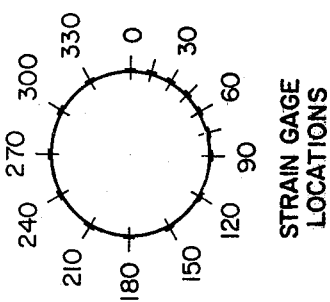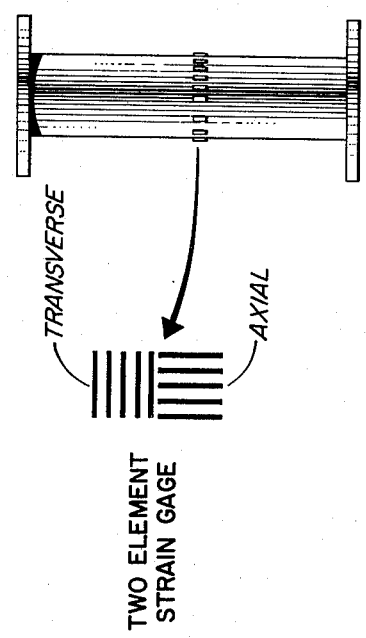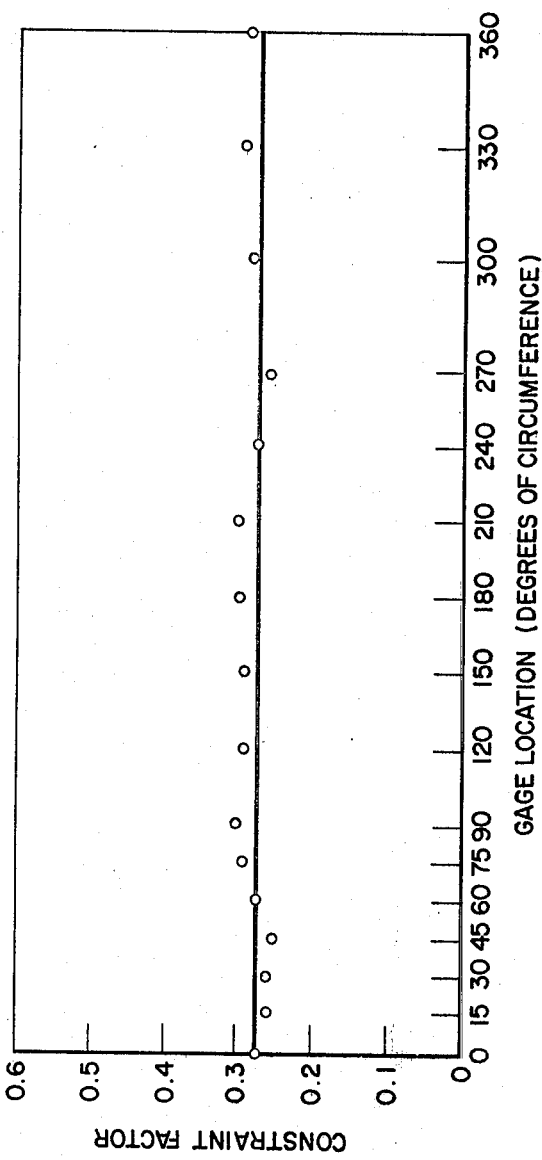

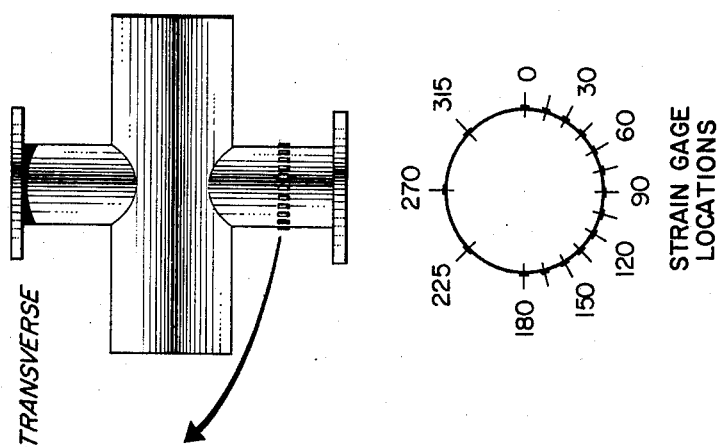
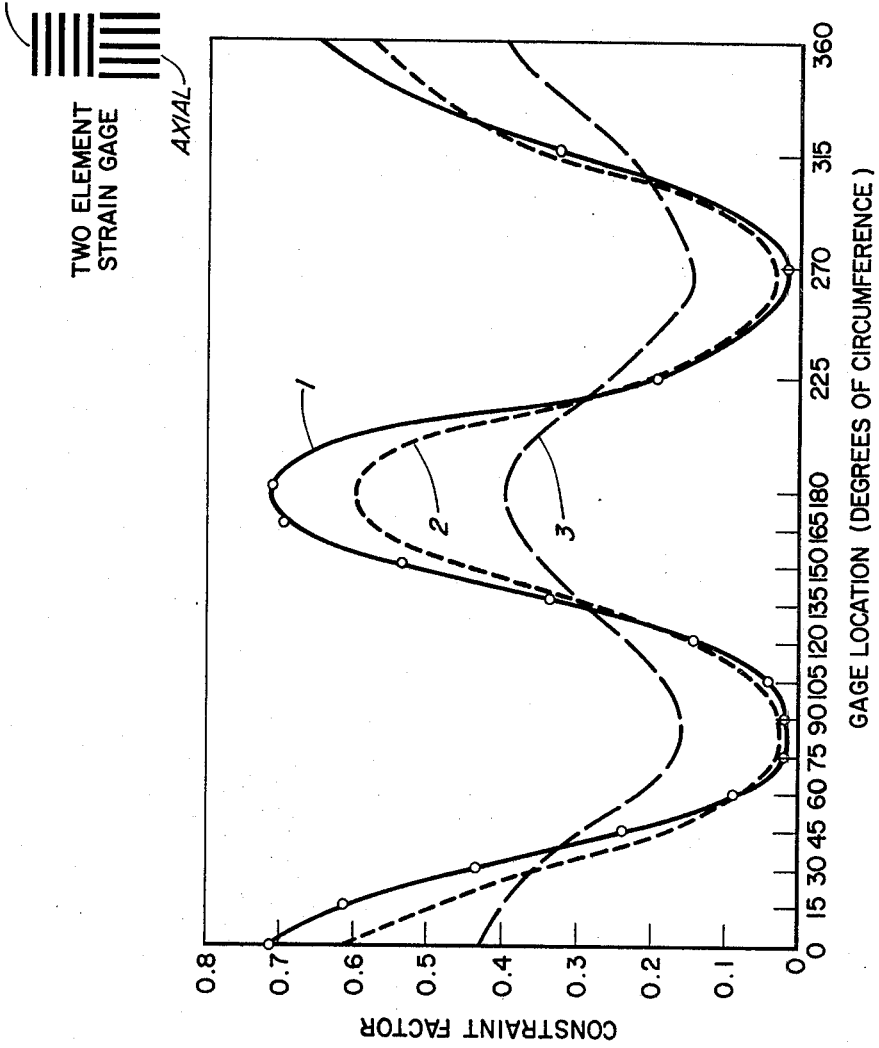

OFFSHORE PLATFORM

CONSTRAINT FACTOR FOR STRUCTURAL MONITORING

This invention relates to a method for predicting structural failure in structural members. In particular, this invention relates to a method for predicting structural failures by monitoring the constraint ratio of structural members.

Failure of structural members subject to stress is a problem of great importance. This is particularly true in metallic structural members of all configurations wherein crack initiation is but the first step leading to total failure of the member. Frame members of aircraft, ships, steel offshore production and drilling platforms and so forth all depend heavily upon metallic structural components. The constant search for more efficient structures places additional stress on structural members. The technology of metallic structural members is constantly being pushed to the limits of the science of metallurgy and engineering designs involved.

There are other examples where structures are subject to stress and which pose potential hazards to the operational safety of the structures and well being of the personnel using them. Examples of these are the rib frames of tankers joined to hull plates, metallic members holding helicopter blades, aircraft frames, frame supports, bridge supports, reactor supports, pressure vessels and the like. All fail with results catastrophic in the loss of human life and equipment, as well as great loss of productivity. It is therefore extremely important that any potential failure in such metallic structural members be detected at the earliest possible point so that appropriate repairs can be made.

Many attempts have been made to detect such failure, the earliest of these attempts being simple visual inspection. More sophisticated systems include the acoustic emission method. However, this method is disadvantageous because equipment is relatively complex and expensive. Ultrasonic methods have been employed but are highly geometry dependent and do not predict crack initiation.

The method described in U.S. Pat. No. 3,667,862 discloses detecting a crack in the wall of a hollow object by evacuating the interior of the hollow object and detecting loss of vacuum. However, this method is not suitable for predicting cracks or for detection of cracks existing in non-permeable structural members. The method also fails to detect a crack until the crack has completely penetrated the member which is being sensed, or to predict crack formation.

U.S. Pat. No. 2,936,612 teaches a quality factor (Q) which decreases prior to failure by rupture upon increase of the amplitude of dynamic strains for structural members. This method is not applicable for the reasons previously set forth and cannot predict failure.

Leaks in vessels can be detected by forming a sealed cavity over suspected leak sight and then placing a vacuum on the cavity to detect a leak by loss of vacuum soap bubbles, or tracer gases. Unfortunately, these methods require ideal conditions in order to be operable, and in addition, will not detect or predict small cracks which do not penetrate a structure.

U.S. Pat. No. 4,145,915 discloses a method for early detection of cracks and non-permeable structural members by placing a fluid tight enclosed patch over the member forming a vacuum within the patch and detecting loss of vacuum when cracks penetrate the patch. Such patches are useful in almost all areas and allow continuous monitoring of structural members without direct human intervention. However, this method likewise does not detect crack initiation outside the patch area.

In many common instances such as aircraft frame members, once a crack has initiated, catastrophic failure can rapidly follow. It would therefore be of great benefit in many applications to be able to predict metallic structural failure, allowing repairs before such catastrophic failure can occur.

It is therefore an object of the pesent invention to provide a method of crack detection and monitoring of crack growth which is not dependent upon fatigue loading. Other objects will become apparent to those skilled in this art as the description proceeds.

In accordance with the present invention, we have discovered a method for predicting structural failure and detecting actual failure in constrained structural members subject to fatigue or static stress comprising placing at least one dual element strain gauge near a structural constraint, said strain gauge having one element extending substantially parallel to the longitudinal axis of the structural member to record longitudinal strain and the second element extending substantially perpendicular to said first element to record transverse strain, then calculating the constraint by determining the ratio of longitudinal strain to transverse strain and monitoring said constraint factor for change. The change can be used to determine structural failure.

The prior art contains references which show crack detection systems using witnessing strain gauges such as described in U.S. Pat. Nos. 3,596,296; 3,136,154 and 3,786,679. Dual element strain gauges themselves are known as shown by U.S. Pat. Nos. 3,088,083; 2,036,458, and 2,626,337. The ratio of values of two element strain gauges are shown in U.S. Pat. Nos. 3,742,760 and 3,210,993. However, none of these systems uses the ratio developed by the strain gauges for any failure monitoring or prediction whatsoever.

U.S. Pat. No. 4,179,940 uses metallurgical readings to determine changes in fatigue strains. This reference requires strain gauges to be placed directly upon a weld or other fastened area. U.S. Pat. No. 3,845,657 shows a system of using strain gauges for detecting cracks in pipe welds. This reference shows that propagation of the new cracks or fissures into the region of at least one welded sensing strain gauge is necessary to provide early warning of imminent failure.

In contrast, the present invention uses at least one 2-element strain gauge having sensing elements 90° to one another. The strain gauge can be installed remotely from intersecting members and a constraint factor is determined. Change in constraint of the structural joint is a result of change in stress in the transverse direction indicating an element or connecting means failure. The present invention thus provides a method of remote sensing of failure and need not concern itself solely with welds but can also monitor adhesive bonding or bolted constrained members. The present invention uses a ratio of transverse to longitudinal strain resulting in a constraint factor to detect lessening of such strain due to a crack or other deterioration of the structural member.

Engineering experience with common elements of modern society such as bridge supports, ship frames, aircraft frames, offshore production platforms and the sort, is sufficiently sophisticated and experienced to predict areas where failure will occur. In the past, such areas have been overbuilt by applying several times more strength in the area than ordinary engineering dictates would show to be necessary. However, as the costs of materials continues to rise while the availability of materials continues to fall, it becomes increasingly necessary to devise a method such that overbuilding is not necessary.

Structural failure arises from a complex of engineering, metallurgical and environmental factors. Service conditions often involve a load spectrum of different stress ranges. Structural elements subject to alternating cycles of tensile strength greater than the endurance limit for a short period exhibits a reduction of the life. When structural elements are subjected to a large number of cycles of stress slightly under the fatigue limit, the resulting fatigue limit is raised. When the amplitude is increased in a series of steps, fatigue life can improve but never completely recover the damage of overstressing.

In most metallurgical structural elements, potential trouble or worry areas are joined areas, whether joined by riveting, overlapping metal plates, or welding. This is particularly true where weld areas such as T-joints or K-joints are used in the structure. In welded joints crack initiation is known to occur most frequently in the heat affected zone (HAZ) immediately surrounding the weld where the metal is normally harder and stronger but less tough than the original metal through the remainder of the member. Such joints form a geometric "constraint" upon the normal strain readings of a steel member. This constraint can be measured by comparing the longitudinal stress to the transverse stress of the member. As long as the constraint ratio remains approximately the same, no failure of either of the structural member or its fastening system has occurred. However, when this ratio begins to change, structural elements have begun to fail.

The instant invention is more concretely described with reference to the drawings below.

BRIEF DESCRIPTION OF THE DRAWINGS

FIG. 1 is a drawing of an unconstrained tubular structural member showing strain gauge locations.

FIG. 3 shows a constrained joined tubular member containing strain gauges at various points about the circumference.

FIG. 4 shows constraint factor as compared to gauge location.

FIG. 7 shows remote sensing of dual element strain gauges mounted on an offshore platform.

DETAILED DESCRIPTION OF THE DRAWINGS

FIG. 1 illustrates placement of two element strain gauges, each containing an axial gauge and a transverse gauge at 90° to one another at various positions about the circumference of an unconstrained tubular structural member under 96,000 pounds of load. In all examples hereafter used, the tubular members were American Petroleum Institute (API) 5-L Grade B pipe. In FIG. 1, 16 dual element strain gauges were placed in locations indicated in FIG. 1 and readings were taken therefrom.

Figure 2:
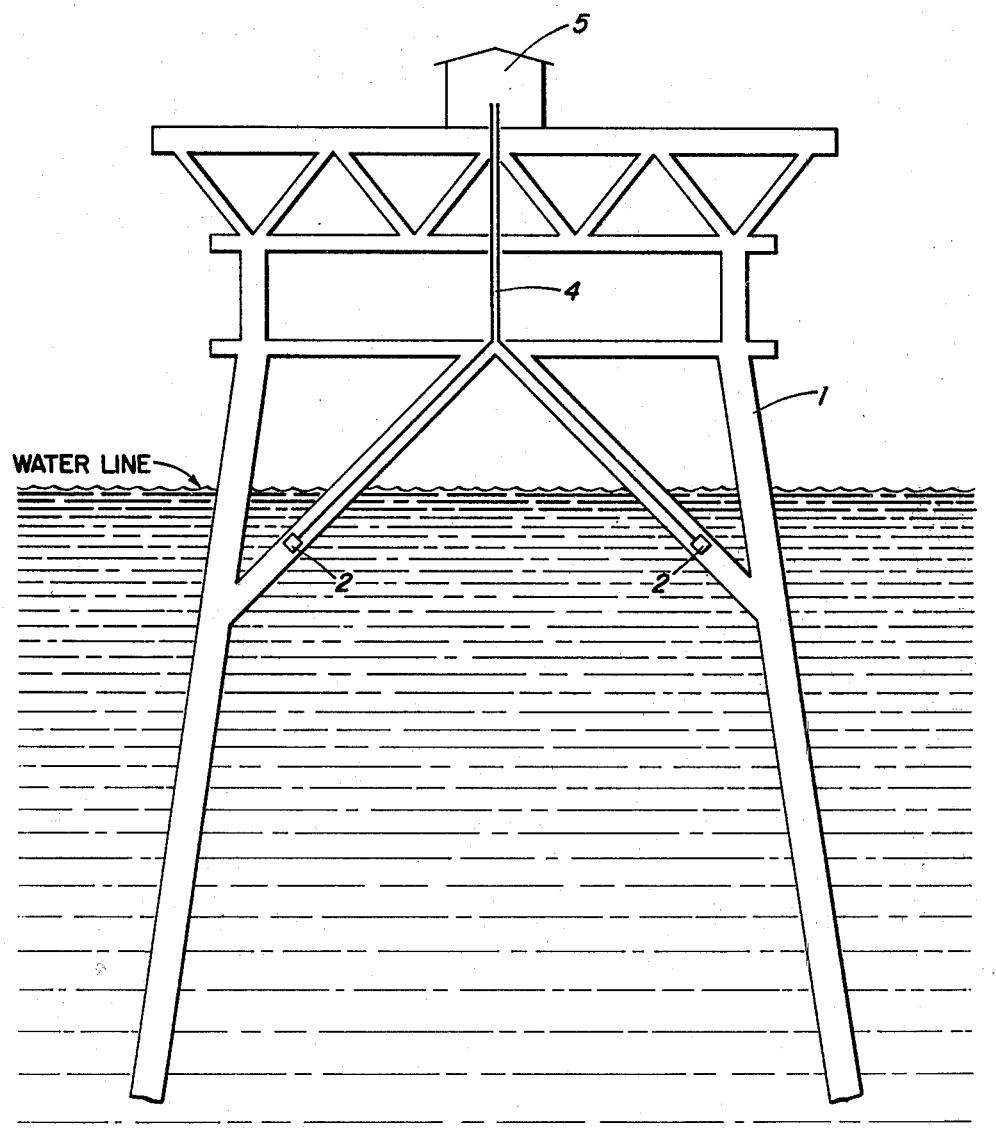
FIG. 2 is a graph showing a constraint factor at various gauge locations for the unconstrained tubular member of FIG. 1.

FIG. 2 illustrates graphically the readings determined from the strain gauge locations of FIG. 1 as a constraint factor. The constraint factor in all figures is the transverse gauge value divided by the axial gauge value. The longitudinal strain measures tensile load and the transverse load strain measures hoop load. These ratios give the values shown in FIG. 2. All values were between 0.25 and 0.30 with an average value of 0.276.

Using such strain gauges all metals give readings between 0.25 and 0.35 depending upon the particular alloy used.

FIG. 3 illustrates a joined section of tubular structural members. The larger member was a 20 inch×1 inch thick API 5-L Grade B pipe. The intersecting smaller diameter pipe was a 10¾ inch×0.500 inch wide API 5-L Grade B pipe. The dual element strain gauge locations were placed about the circumference of the smaller pipe as indicated. This structural joint was then placed under a load of ±96,000 pounds.

FIG. 4 is the constraint factor of the constrained pipe joint. Graph 1 indicates a base line of the sound sample under the constrained joint. Graph 2 shows the constraint factor data after crack initiation in the constrained joint. Graph 3 shows the constraint factor after severe cracking nearing failure. Total failure would of course approach the unconstrained load of FIG. 2.

After the Graph 3 data had been obtained, the induced crack was repaired by welding and a reading was taken. Graph 1 of FIG. 4 was duplicated, showing the effectiveness of the present invention for returning to constrained values.

Figure 5:
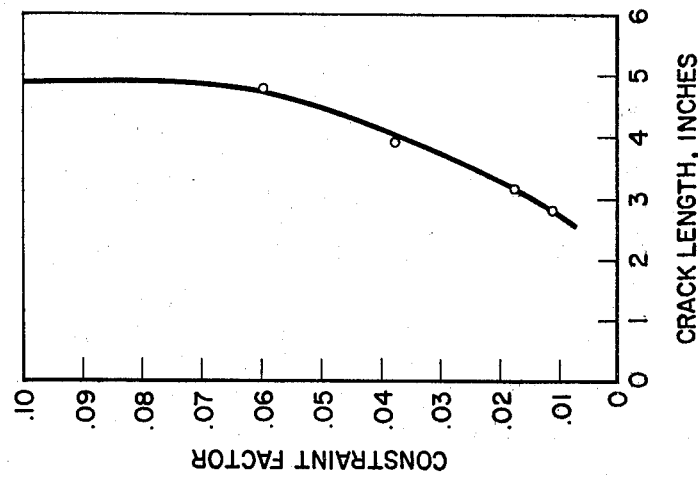
FIG. 5 shows a comparison of crack length in inches to constraint factor.

FIG. 5 shows a constraint factor as opposed to crack length in inches. It can be seen that the constraint factor increases exponentially as the crack length grows. Amplitude between the high and low readings indicates the severity of failure.

Figure 6:
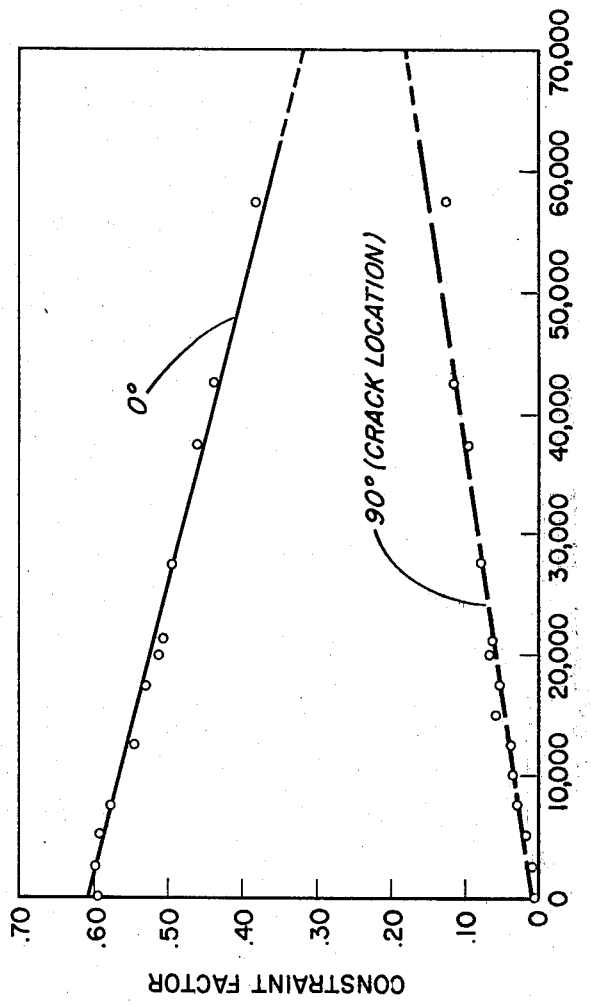
FIG. 6 shows a constraint factor at two different locations as compared to stress cycles.

FIG. 6 shows the constraint factor as compared to stress cycles using readings from two locations, 0° and 90°. A crack was initiated at 90° and the constraint factor was compared. It can be seen that the opposite readings tend to converge as the failure progresses.

FIG. 7 shows an offshore platform (1) having affixed thereto a multiplicity of dual element strain gauges (2), which are optionally enclosed in environmental patches. The strain gauges are monitored using remote sensing means (4), usually wire or cables, and are detected using a convenient remote data collection system (5). Such a data collection system is preferably capable of monitoring any strain gauge at will, recording readings continuously for all gauges, and activating an alarm when preselected constraint ratios are reached or exceeded.

According to our invention, strain gauges are provided at locations on structural members which will provide either a high or a low reading as determined by the FIG. 4. Such locations can be determined easily by experience or by experimentation. For example, in the 90° joint shown, a gauge located at either 0° or 90° will adequately indicate the constraint factor. A 0° gauge will indicate a higher constraint factor which will tend to decrease with loss of constraint or failure. The gauge located at the 90° location will tend to increase with loss of constraint or failure. In either case, however, the change is the important element. While two or more gauges can be used, only one is necessary. Such gauges are normally placed on the structural member in an area of highest constraint at a distance of from about 1 to 2 structural member diameters from the constrained area. However, such distance is optional and can be varied substantially. Such strain gauges can then be monitored continuously or periodically and the constrained factor compared to the original constrained factor. This ratio is calculated by the difference between the constraint factor and the original reading. For example, in most metals a ratio of 0.30 is average, so the difference is calculated by $$\frac{C_f - .30}{.30}$$

Of course, the actual unconstrained ratio would normally be used, especially when structural materials other than metals are involved. Normally, a factor differing about 50% or more will indicate that failure has begun or is imminent. In a continuous monitoring system such a change would then signal an alarm.

Although the instant invention is illustrated with respect to tubular members, other structural members, such as I-beams, square welded members, and so forth can be monitored. The constraint factor will not be of the same value as for a tubular member, but will none the less be useful since only the change in original constrained ratio is used to detect actual failure or imminent failure.

The method of the present invention is also applicable to materials other than steel. Structural members comprised of fiberglass, wood, concretes and the like can also be monitored. Such structural members are well known, and failure of these materials can be as catastrophic to a structure as failure of a steel structure. The cross-sectioned configuration of such members is likewise not critical.

The gauges should be located in the area of highest constraint. Such areas can be determined by experienced personnel by inspection of the structural arrangement, but can also be determined experimentally as described in the figures by using more than one dual element strain gauge then removing all but those in the area of highest or lowest reading. The area of highest or lowest reading is preferred in order to give maximum resolution to the present invention. However, it will be apparent to those skilled in this art that gauges placed at positions other than the highest and lowest will still provide some benefit as a change can be monitored. However, the degree of change will not be as severe and thus the resolution of the method would not be as high.

Strain gauges useful in the practice of the present invention are those well known in the art. Such strain gauges can range in size and gauge length from microdots (0.2) to over 6 inches in length. The particular gauge will, of course, be chosen for the application necessary. Representative examples of suitable gauges are those sold by Micro. Measurements, Romulus Michigan, Type EA-06-125-TQ-350 (0.125 in gauge length) and William T. Bean Co., Detroit Michigan Type TA-BAB-06-125 TA-350 as well as other well known suppliers of strain gauges.

Groups are preferably placed so as to exclude ambient environment. This can be accomplished by any means known to the art. Preferred methods excluding environment are those described in U.S. Pat. Nos. 4,143,546, and 4,135,386.

Strain gauges are normally affixed to structural members using an adhesive such as epoxy. These adhesives are extremely suitable for use in affixing the patches covering the strain gauges to the structural members. Strain gauges themselves are normally applied to the structural members by any means well known to those skilled in this art such as by adhesive or welding.

Strain gauges, comparators, and warning means can be incorporated conveniently into single consoles having the capability for monitoring many channels, as well as independent strain gauges, simultaneously. In addition, such systems can make automatic comparisons of each individual strain gauge reading and note which ones are changing in value to indicate changing constraint.

Thus the present invention describes a method for predicting structural failure and detecting actual failure in constrained structural members subject to fatigue and static stress comprising placing at least one dual element strain gauge near a structural constraint wherein one element extends substantially parallel to the longitudinal axis of the structural member to record longitudinal strain (axial load) and the second element extends substantially perpendicular to the first element to record transverse strain (hoop load) wherein said placement is preferably determined by a maximum or minimum reading from either element of said gauge; then calculating the constraint factor of said structural member by determining the ratio of longitudinal strain to transverse strain and monitoring the factor for change, such change indicating structural failure. The present invention is applicable to systems containing aluminum and titanium metals as well, although such systems will have different initial readings than those containing iron or steel alloys. The structural members can be constrained by welding, bolting, adhesives, or any desired method and still be susceptible to tests using the instant invention.

While certain embodiments and details have been shown for the purpose of illustrating this invention, it will be apparent to those skilled in this art that various changes and modifications may be made herein without departing from the spirit or scope of the invention.

We claim:

1. A method for predicting structural failure and detecting axial failure in constrained structural members subject to fatigue and static stress comprising
   (a) placing at least one dual element strain gauge near a structural constraint, said strain gauge having one element extending substantially parallel to the longitudinal axis of the structural member to record longitudinal strain, and the second element extending substantially perpendicular to said first element to record transverse strain, wherein said placement is determined by a maximum or minimum reading from either element of said gauge;
   (b) calculating a constraint factor of said structural member by determining the ratio of longitudinal strain to transverse strain, then
   (c) monitoring said factor for change, said change indicating structural failure.

2. A method as described in claim 1 wherein the structural members are comprised of metallic members.

3. A method as described in claim 2 wherein a plurality of dual element strain gauges are placed on structural members.

4. A method as described in claim 3 wherein strain gauges are positioned on structural members in the area of highest constraint.

5. A method as described in claim 3 wherein said strain gauges are monitored continuously.

6. A method as described in claim 5 wherein constraint factors are continuously compared to original constraint factors.

7. A method as described in claim 6 wherein the strain gauges are placed from 1 to 2 structural member diameters from the constrained area.

8. A method as described in claim 7 wherein the structural members are welded.

9. A method as described in claim 7 wherein the structural members are bolted.

10. A method as described in claim 7 wherein the strain gauges are protected from the structural member environment.

11. A method as described in claim 7 wherein the only one dual element strain gauge is monitored for change in constraint factor.

12. A method as described in claim 7 wherein crack growth is monitored by comparing constraint factor change.

13. A method as described in claim 7 wherein structural integrity is monitored with sensing elements remote from areas of failure.

14. A method as described in claim 7 wherein the constraint factor change of 50% or more will signal an alarm.

15. A method as described in claim 14 wherein the structural member is part of an offshore platform.

16. A method as described in claim 1 wherein the structural members are comprised of fiberglass.

17. A method as described in claim 1 wherein the structural members are comprised of wood.

18. A method as described in claim 1 wherein the structural members are comprised of concrete.

* * * * *